(12) United States Patent
Ason et al.

(10) Patent No.: US 10,196,430 B2
(45) Date of Patent: Feb. 5, 2019

(54) EFFECTIVE USE OF YEAST AND YEAST EXTRACT RESIDUE

(71) Applicant: KOHJIN LIFE SCIENCES CO., LTD., Tokyo (JP)

(72) Inventors: Kenichi Ason, Oita (JP); Yusuke Fukuda, Oita (JP); Setsuko Hirakura, Nagasaki (JP); Hiroko Kodera, Oita (JP); Eiji Nakao, Oita (JP)

(73) Assignee: KOHJIN LIFE SCIENCES CO., LTD., Tokyo (JP)

( * ) Notice: Subject to any disclaimer, the term of this patent is extended or adjusted under 35 U.S.C. 154(b) by 180 days.

(21) Appl. No.: 14/355,028

(22) PCT Filed: Oct. 31, 2012

(86) PCT No.: PCT/JP2012/078160
§ 371 (c)(1),
(2) Date: Apr. 29, 2014

(87) PCT Pub. No.: WO2013/065732
PCT Pub. Date: May 10, 2013

(65) Prior Publication Data
US 2014/0308430 A1 Oct. 16, 2014

(30) Foreign Application Priority Data

Oct. 31, 2011 (JP) .................................. 2011-239004
Oct. 15, 2012 (JP) .................................. 2012-228046
Oct. 15, 2012 (JP) .................................. 2012-228047

(51) Int. Cl.
| | | |
|---|---|---|
| A23L 1/28 | (2006.01) | |
| C07K 14/39 | (2006.01) | |
| A23J 1/18 | (2006.01) | |
| C07K 14/395 | (2006.01) | |
| C12N 1/18 | (2006.01) | |
| C12N 1/16 | (2006.01) | |
| C12P 21/06 | (2006.01) | |
| A23L 27/24 | (2016.01) | |
| A23L 33/145 | (2016.01) | |

(52) U.S. Cl.
CPC .............. C07K 14/39 (2013.01); A23J 1/18 (2013.01); A23L 27/24 (2016.08); A23L 33/145 (2016.08); C07K 14/395 (2013.01); C12N 1/16 (2013.01); C12N 1/18 (2013.01); C12P 21/06 (2013.01)

(58) Field of Classification Search
CPC . A23L 1/23; A23L 1/18; A23L 33/145; A23L 27/24; C07K 14/39; C07K 14/395; C12N 1/16; C12N 1/18; C12P 21/06
USPC ................... 426/62, 534, 650, 656
See application file for complete search history.

(56) References Cited

U.S. PATENT DOCUMENTS

| | | | | |
|---|---|---|---|---|
| 4,032,663 A | * | 6/1977 | Kobayashi | ............. A23B 7/155 426/51 |
| 4,962,094 A | | 10/1990 | Jamas et al. | |
| 6,020,324 A | | 2/2000 | Jamas et al. | |
| 2002/0155126 A1 | | 10/2002 | Shirasu et al. | |
| 2011/0045545 A1 | | 2/2011 | Yu et al. | |

FOREIGN PATENT DOCUMENTS

| | | | |
|---|---|---|---|
| EP | 0566347 | | 4/1993 |
| EP | 2272876 | * | 1/2011 |
| JP | 52-076424 | | 6/1977 |
| JP | 61-092589 | | 5/1986 |
| JP | 01-144956 | | 6/1989 |
| JP | 02-219560 | | 9/1990 |
| JP | 04-144667 | | 5/1992 |
| JP | 04-505997 | | 10/1992 |
| JP | 5-252894 | | 10/1993 |
| JP | 7-184640 | | 7/1995 |
| JP | 9-56361 | | 3/1997 |
| JP | 9-103266 | | 4/1997 |
| JP | 09-117263 | | 5/1997 |
| JP | 10-57091 | | 3/1998 |
| JP | 2001-55338 | | 2/2001 |
| JP | 2001-178398 | | 7/2001 |
| JP | 2002-153263 | | 5/2002 |
| JP | 2004-113246 | | 4/2004 |
| JP | 2005-102549 | | 4/2005 |
| JP | 2006-014719 | | 1/2006 |
| JP | 2006-94757 | | 4/2006 |
| JP | 2007-006838 | | 1/2007 |

(Continued)

OTHER PUBLICATIONS

JP 01-144956, Jun. 1989, translation.*
JP 02-219560, Sep. 1990, translation.*
JP 52-76424, Jun. 1997, translation.*
U.S. Appl. No. 14/112,142 to Toshiya Sato et al., filed Oct. 16, 2013.
U.S. Appl. No. 14/240,834 to Yoshie Yasumatsu et al., filed Feb. 25, 2014.
International Search Report issued Dec. 11, 2012 in PCT/JP2012/078160.

*Primary Examiner* — Leslie A Wong
(74) *Attorney, Agent, or Firm* — Greenblum & Bernstein, P.L.C.

(57) ABSTRACT

To provide effective use from a yeast extract residue, an excess of which is produced as a byproduct of yeast extract, or reduction in amount of the yeast extract residue. Also to obtain various useful substances. A cell wall lytic enzyme having no protease is allowed to act on a yeast extract residue, after which a heat treatment is performed at 70 to 80° C. for 10 to 20 minutes, thereby enabling separation into a fraction of primarily cell walls and a fraction of primarily protein. A yeast protein having a protein content of 60% or more is obtained from the fraction of primarily protein and, by subjecting the yeast protein to enzymatic degradation, a seasoning having a high amount of total nitrogen is obtained.

6 Claims, No Drawings

(56) References Cited

FOREIGN PATENT DOCUMENTS

| | | | |
|---|---|---|---|
| JP | 2007-274910 | | 10/2007 |
| JP | 2009-022227 | | 2/2009 |
| JP | 2010-533479 | | 10/2010 |
| JP | 2011-205927 | | 10/2011 |
| JP | 6-113789 | | 4/2014 |
| WO | WO 90/04334 | * | 5/1990 |

* cited by examiner

EFFECTIVE USE OF YEAST AND YEAST EXTRACT RESIDUE

FIELD OF THE INVENTION

The present invention relates to a new food ingredient obtained by allowing a specific enzyme to act on yeast cell bodies from which yeast extract has been extracted. Specifically, the present invention relates to a yeast protein having a high protein content, a cell wall fraction having a high dietary fiber content, and a seasoning having a high nitrogen content.

BACKGROUND OF THE INVENTION

Yeast contains nutritive components and abundant taste components such as nucleic acids, amino acids, and peptides. Yeast extract, which is an extract thereof, is used in a broad range of fields, such as in natural seasonings and health foods, and as a culture for microscopic organisms. Various methods of producing yeast extract are known which use extracting enzymes, mediums, and the like. Examples include the method of Patent Literature 1.

Yeast cell bodies in which yeast extract has been extracted from yeast have, as principal components, a cell wall component of glucan, mannan, and the like; and proteins; lipids; and the like. There are several known publications regarding processing and methods of effectively using these yeast cell bodies. For example, Patent Literature 2 teaches a method of treating a yeast extract extraction residue solubilized using a specific enzyme in waste water treatment. Patent Literature 3 describes a method of producing mannose by causing yeast cell bodies of a yeast extract extraction residue to be assimilated by microorganisms. Patent Literature 4 describes a method of obtaining a medicinal compound by alkali treatment of a yeast cell body residue from which yeast extract has been extracted, followed by irrigation thereof. Patent Literature 5 describes a method of obtaining a microorganism culture substrate material by allowing a cell wall lytic enzyme or the like to act on yeast cell bodies from which yeast extract has been extracted.

However, due to products having a low added value relative to processing costs, or due to a low amount of consumption of yeast extract extraction residue in each application, none of these methods have been put into practice or managed to dramatically reduce an amount of yeast extract residue.

There are also reports, as in Patent Literature 6, focusing on dietary fiber contained in the yeast cell wall fraction from which yeast extract has been extracted. Dietary fiber or a composition including a large amount thereof is presently in use in a variety of applications such as as a functional ingredient in health food or foodstuff, as a physicality enhancer, and the like. Glucan and mannan contained in the yeast cell wall are refined using various methods and are widely utilized as a health food, a functional ingredient, animal feed, and the like. In particular, β-1,3-1,6-glucan has many functions that are being widely studied throughout the world, such as an antitumor effect, an immunostimulator effect, and the like. In recent years, extremely low molecular weight β-1,3-1,6-glucan has been reported to have an antioxidant effect as well. In addition, mannose, which is refined from mannan, has also received attention as a functional food. However, when used as-is, a yeast cell wall composition (as a yeast extract extraction residue) has many impurities and a low dietary fiber content. Therefore, Cited Reference 6 describes the necessity of chemical treatments such as alkali ethanol treatment, alkali/acid treatment, and the like; and physical treatments such as homogenization as methods to remove impurities. Chemical methods such as alkali ethanol treatment and alkali/acid treatment are unlikely to be put into actual use due to questions of food safety and because a great quantity of drugs are produced as waste products. Meanwhile, homogenization treatment uses costly machinery and equipment, and is also unlikely to be put into actual use. Besides these chemical and physical methods, methods utilizing enzymes have also been investigated. However, yeast cell walls are primarily composed of the dietary fibers glucan and mannan as well as protein and lipids, which form strong and complex conjugates. Therefore, the yeast extract residue is not particularly susceptible to the action of a typical enzyme, and even when susceptible the yeast extract residue is unlikely to break down, making it difficult to increase dietary fiber content any further without chemical methods or mechanical pulverization.

Given the above, there is currently little value in using great quantities of yeast cell bodies from which yeast extract has been extracted, which is produced as part of the production of yeast extract. A remainder utilized as fertilizer and animal feed and the like is currently treated as industrial waste.

Additionally, Patent Literature 7 describes being able to obtain a savory seasoning by hydrochloric acid hydrolysis or enzymatic degradation of protein from, for example, livestock meat, fish meat, soy beans, wheat, or corn.

RELATED ART

Patent Literature

Patent Literature 1: Japanese Patent Laid-open Publication No. H5-252894, Japanese Patent Laid-open Publication No. H6-113789, Japanese Patent Laid-open Publication No. H9-56361

Patent Literature 2: Japanese Patent Laid-open Publication No. H7-184640

Patent Literature 3: Japanese Patent Laid-open Publication No. H10-57091

Patent Literature 4: Japanese Patent Laid-open Publication No. 2001-55338

Patent Literature 5: Japanese Patent Laid-open Publication No. 2007-006838

Patent Literature 6: Japanese Patent Laid-open Publication No. H9-103266, Japanese Patent Laid-open Publication No. 2004-113246, Japanese Patent Laid-open Publication No. H9-117263, Japanese Patent Laid-open Publication No. 2002-153263

Patent Literature 7: Japanese Patent Laid-open Publication No. 2001-178398, Japanese Patent Laid-open Publication No. 2006-94757

SUMMARY OF THE INVENTION

Problems to be Solved by the Invention

An objective to be solved is effective use of yeast cell bodies from which yeast extract has been extracted, an excess of which is produced as a byproduct of yeast extract, or effective use of cultured yeast cell bodies which do not yield yeast extract. Another objective to be solved is to obtain a composition derived from yeast cell bodies with a high content of a useful component.

Means for Solving the Problems

The inventors of the present invention have, as a result of their research, discovered that a composition having a high content of yeast-derived protein (hereafter referred to as "yeast protein") and a cell wall fraction having a high dietary fiber content can be produced by allowing a cell wall lytic enzyme having no protease to act on yeast cell bodies from which yeast extract has been extracted, then applying a heat treatment after the action of the cell wall lytic enzyme. Moreover, the inventors of the present invention have discovered that a seasoning having a high nitrogen content can be obtained by allowing protease to act on the yeast protein, and that in addition to the seasoning having an intense savory flavor, the seasoning has a distinctive flavor not found in various conventional protein hydrolysates. Furthermore, even in a case of an enzyme where the cell wall lytic enzyme contains protease, by allowing the enzyme to act at a temperature or pH where the protease is not active, yeast protein of corresponding quality and a cell wall fraction having high dietary fiber content can be produced. In addition, even in a case where the cell wall lytic enzyme is allowed to act on cultured yeast that has not undergone extraction, rather than on yeast cell bodies from which yeast extract has been extracted, yeast protein and a cell wall fraction of corresponding quality can be produced.

Specifically, the present invention relates to:

(1) A yeast protein obtained from yeast cell bodies from which yeast extract has been extracted or yeast cell bodies that have not undergone yeast extract extraction, the yeast protein having a protein content of 60% or more;

(2) A yeast-derived seasoning produced by enzymatic degradation of a yeast protein obtained from yeast cell bodies from which yeast extract has been extracted or yeast cell bodies that have not undergone yeast extract extraction, the yeast protein having a protein content of 60% or more, the yeast-derived seasoning having a total nitrogen content in a solid content of 11% or more;

(3) A manufacturing method of (1) or (2) in which a cell wall lytic enzyme is allowed to act on yeast cell bodies from which yeast extract has been extracted or yeast cell bodies that have not undergone yeast extract extraction, after which a cell wall structural component is eliminated and yeast protein is obtained;

(4) A manufacturing method of a yeast cell wall fraction containing 50 wt % or more of dietary fiber, in which manufacturing method a cell wall lytic enzyme is allowed to act on yeast cell bodies from which yeast extract has been extracted or yeast cell bodies that have not undergone yeast extract extraction, after which a fraction of primarily protein is removed;

(5) The manufacturing method of the yeast protein or the yeast cell wall fraction according to (3) or (4) in which the cell wall lytic enzyme is a glucanase having no protease;

(6) The manufacturing method of the yeast protein or the yeast cell wall fraction according to (3) to (5) in which the glucanase is *Streptomyces*-derived;

(7) The manufacturing method of the yeast protein or the yeast cell wall fraction according to (3) to (6) in which the cell wall lytic enzyme is allowed to act at a temperature where the protease is not active or at a pH where the protease is not active;

(8) The manufacturing method of the yeast protein or the yeast cell wall fraction according to any one of (3) to (7) in which, following the action of the cell wall lytic enzyme, a heat treatment is performed at 50° C. or more, preferably at 70 to 80° C., for five minutes or more, preferably for 10 to 20 minutes, after which the cell wall structural component is removed; and (9) The yeast cell wall fraction obtained with the method according to any one of (4) to (8) in which a β-1,3-1,6-glucan content is 80 wt % or more.

Effect of the Invention

Utilizing the present invention, yeast cell bodies from which yeast extract has been extracted, which have conventionally been an industrial waste product or low-cost fertilizer and animal feed, as well as yeast cell bodies discarded in a beer manufacturing process which cannot be used for yeast extract can be effectively used for yeast protein, high dietary fiber compositions, and seasoning without requiring expensive equipment or chemical treatments, making possible a significant reduction in waste. The yeast protein obtained has a high protein content and a low allergenicity, and therefore can also be used as a substitute for wheat or soy proteins. In addition to being an ingredient in health foods, the yeast protein is favorable as a raw material for manufacture of food and seasoning. The high dietary fiber composition obtained is a food with a high degree of safety, and therefore can also be used in a food physicality enhancer and the like, in addition to being an ingredient in health foods. Moreover, the seasoning obtained by an action of a protease on the yeast protein has a solid content with a total nitrogen content of 11% or more; has richness; has a favorable flavor that is different from other protein hydrolysates and unique to seafoods; and can be used as a new type of seasoning.

MODE FOR CARRYING OUT THE INVENTION

Hereafter, a concrete description of the present invention is given. Yeast in the present invention can be dissolved by a yeast cell wall lytic enzyme. Examples include fungi belonging to genera such as *Saccharomyces, Endomycopsis, Saccharomycodes, Nematospora, Candida, Torulopsis, Brettanomyces,* and *Rhodotorula*; or can include so-called brewer's yeast, baker's yeast, sake yeast, and the like. Of these, *Saccharomyces cerevisiae* or *Candida utilis* are preferably used as raw material for the yeast extract.

Examples of the yeast cell bodies of the present invention include primarily yeast cell bodies from which yeast extract has been extracted (i.e., yeast extract residue). The yeast cell bodies from which yeast extract has been extracted are, specifically, a residue left after the yeast extract has been removed from the yeast by an extraction process using one or more of hot water, alkaline solution, autolysis, mechanical pulverization, a cell wall lytic enzyme, a protease, ribonuclease, or deaminase. Examples include "KR yeast" manufactured by Kohjin Co., Ltd. Such residue is typically primarily composed of glucan, mannan, protein, and lipids. Structurally, the glucan, mannan, and other components form a conjugate and are expected to form strong bonds such that even direct contact with protease has almost no effect.

An additional example of yeast cell bodies likely to be utilized in actual production is yeast cell bodies which cannot be used for yeast extract. Examples may include yeast cell bodies for fertilizer and animal feed, which are discarded in a beer manufacturing process, and waste yeast cell bodies. Moreover, the yeast protein obtained from such yeast cell bodies that have not undergone yeast extract extraction has a lower relative protein content when compared to the yeast protein of yeast cell bodies from which yeast extract has been extracted.

Obtaining the yeast protein according to the present invention involves first adding water to the above-noted yeast cell bodies and adjusting a concentration of a suspension thereof to approximately 5 to 20%, after which a cell wall lytic enzyme is added and allowed to act at 30° C. or more for one to six hours.

Examples of the cell wall lytic enzyme added herein include glucanase and mannanase, but in the present invention it is important that the cell wall lytic enzyme have almost no protease activity. Specific examples include a *Streptomyces*-derived β-glucanase "Denatyme GEL" (manufactured by Nagase ChemteX Corporation) and a *Taloromyces*-derived β-glucanase "Filtrase BRX" (manufactured by DSM Japan), of which the "Denatyme GEL" is most preferred. "Tunicase FN" manufactured by Amano Enzyme Inc. is an enzyme preparation which is a mixture of glucanase and protease. When an enzyme preparation containing protease such as this is used, the enzyme preparation must be allowed to act at a temperature or pH where the protease within the enzyme preparation is not active.

Following the reaction using the cell wall lytic enzyme, a heat treatment is performed at a temperature of 50° C. or more, preferably between 50 and 100° C., and more preferably between 70 and 80° C. for five minutes or more, and preferably between 10 and 20 minutes, after which cell wall structural components are removed by a centrifuge and a fraction of primarily protein is obtained. The fraction of primarily protein is taken as-is or is dried to obtain yeast protein. Moreover, when the above-described heat treatment is not performed, yeast protein yield from the source fungal bodies decreases. Therefore, this is not preferred from a cost perspective.

Yeast cell bodies that have not undergone yeast extract extraction and yeast cell bodies from which yeast extract has been extracted can both be used as the raw material of the yeast protein according to the present invention. The yeast protein obtained by the above method using yeast cell bodies that have not undergone yeast extract extraction as the raw material has a protein content of 60% or more. Meanwhile, the yeast protein obtained by the above method using yeast cell bodies from which yeast extract has been extracted as the raw material has a protein content of 80% or more and can be favorably utilized as an ingredient in health foods, as a raw material for manufacture of food and seasoning, or the like.

Meanwhile, the cell wall structural components removed by the centrifuge are fractions primarily composed of dietary fiber. These fractions are taken as-is or are concentrated and then dried to obtain a yeast cell wall fraction. When the heat treatment is not performed prior to centrifugation, yeast cell wall fraction yield from the source fungal bodies decreases.

The yeast cell wall fraction produced by the above method using yeast cell bodies from which yeast extract has been extracted as the raw material has a dietary fiber content of 50 wt % or more in the dried product. Therefore, the high dietary fiber composition can be used as an ingredient in health foods, a food physicality enhancer, and the like. Moreover, by processing the yeast cell wall fraction with a separation filtration membrane having an appropriate molecular weight cut-off, a yeast cell wall fraction having a β-1,3-1,6-glucan content of 80 wt % or more can be obtained.

In comparison, seasoning can be obtained with the yeast protein as a raw material. Water is added to the above-noted dried product of the yeast protein and a suspension thereof is adjusted to a concentration of approximately 5 to 15%, after which a protease is added and allowed to act at 30° C. or more for three to ten hours, then centrifugal separation is performed. An obtained supernatant is a seasoning that includes a large amount of a savory component primarily composed of amino acid. Moreover, the supernatant can be concentrated and spray-dried as needed to obtain a powdered seasoning.

The seasoning produced by the above method using yeast cell bodies as the raw material has a high total nitrogen content of 11% or more; is particularly rich in peptides; has richness: and has a distinct and favorable flavor of mellowed fish sauce. The flavor is unique, differing from various savory seasonings obtained by hydrochloric acid hydrolysis or enzymatic degradation of various conventional protein hydrolysates, specifically proteins such as livestock meat, fish meat, soy beans, wheat, corn, and the like. A field of use for the seasoning is often for favorable use as a liquid preparation or an ingredient thereof, similar to a so-called protein enzymolysis product and a hydrochloric acid hydrolysate, but the field of use is not particularly limited. The seasoning can also be broadly used in processed foods.

EMBODIMENTS

Hereafter, a concrete description of the present invention is given using embodiments.

Embodiment 1

In the method of producing *Candida utilis* yeast extract according to embodiment 3 of Japanese Patent Laid-open Publication No. 2002-101846, after extraction of the yeast extract, a fungal body residue removed by centrifugation was obtained and used as raw material yeast cell bodies. One kilogram of these yeast cell bodies were suspended in water at a concentration of 10%, then were adjusted to 40° C. and a pH of 4.5, after which 30 g of a cell wall lytic enzyme ("Filtrase BRX," manufactured by DSM Japan) was added to the suspension and allowed to act for five hours. The suspension was then heat treated at 70° C. for 20 minutes, after which it was separated by a centrifuge into a fraction of primarily cell walls and a fraction of primarily protein. The fraction of primarily protein was dried to obtain 611 g of yeast protein. Protein content of this yeast protein was measured using the Kjeldahl method to give a protein content of 72%. Meanwhile, the fraction of primarily cell walls was dried to obtain 186 g of a yeast cell wall fraction. Dietary fiber content of this yeast cell wall fraction was measured using an enzymatic-gravimetric method (Japan Food Research Laboratories value) to give a dietary fiber content of 58%.

Embodiment 2

One kilogram of "KR yeast" (manufactured by Kohjin Co., Ltd.) yeast cell bodies from which *Candida utilis* yeast extract has been extracted were suspended in water at a concentration of 10%, then were adjusted to 40° C. and a pH of 6.0, after which 3 g of a cell wall lytic enzyme ("Denatyme GEL," manufactured by Nagase ChemteX Corporation) was added to the suspension and allowed to act for five hours. The suspension was then heat treated at 70° C. for 20 minutes, after which it was separated by a centrifuge into a fraction of primarily cell walls and a fraction of primarily protein. The fraction of primarily protein was dried to obtain 706 g of yeast protein. Protein content of this yeast protein was measured using the Kjeldahl method to give a protein content of 84%. Meanwhile, the fraction of primarily cell walls was dried to obtain 318 g of a yeast cell wall fraction. Dietary fiber content of this yeast cell wall fraction was measured using an enzymatic-gravimetric method (Japan Food Research Laboratories value) to give a dietary fiber content of 61%. The yeast protein obtained was adjusted to a concentration of 10% in water suspension, then was adjusted to 45° C. and a pH of 8.0, after which 7 g of a protease (PROTIN NY-100, manufactured by Amano Enzyme Inc.) was added to the suspension and allowed to act for five hours. A residue was then removed by centrifugation and the supernatant obtained was concentrated and spray dried to obtain 500 g of a powdered seasoning of primarily amino acids. Nitrogen content of this seasoning was measured using the Kjeldahl method to give 14.1%.

Embodiment 3

One kilogram of "Yeast MG" (manufactured by Kohjin Co., Ltd.) *Candida utilis* culture yeast cell bodies were suspended in water at a concentration of 10%, then were adjusted to 40° C. and a pH of 6.0, after which 3 g of a cell wall lytic enzyme ("Denatyme GEL," manufactured by Nagase ChemteX Corporation) was added to the suspension and allowed to act for five hours. The suspension was then heat treated at 70° C. for 20 minutes, after which it was separated by a centrifuge into a fraction of primarily cell walls and a fraction of primarily protein. The fraction of primarily protein was dried to obtain 320 g of yeast protein. Protein content of this yeast protein was measured using the Kjeldahl method to give a protein content of 72%.

Embodiment 4

One kilogram of "Yeast MG" (manufactured by Kohjin Co., Ltd.) *Candida utilis* culture yeast cell bodies were suspended in water and heat treated at 90° C. for 20 minutes. A residue left after extracting an extract portion with a centrifuge was suspended in water at a concentration of 10%, then was adjusted to 40° C. and a pH of 6.0, after which 3 g of a cell wall lytic enzyme ("Denatyme GEL," manufactured by Nagase ChemteX Corporation) was added to the suspension and allowed to act for five hours. The suspension was then heat treated at 70° C. for 20 minutes, after which it was separated by a centrifuge into a fraction of primarily cell walls and a fraction of primarily protein. The fraction of primarily cell walls was then dried to obtain 256 g of a yeast cell wall fraction. Dietary fiber content of this yeast cell wall fraction was measured using an enzymatic-gravimetric method (Japan Food Research Laboratories value) to give a dietary fiber content of 56%.

Embodiment 5

One kilogram of dried fungal bodies of brewer's yeast derived from *Saccharomyces cerevisiae* culture yeast were suspended in water at a concentration of 10%, then were adjusted to 40° C. and a pH of 6.0, after which 3 g of a cell wall lytic enzyme ("Denatyme GEL," manufactured by Nagase ChemteX Corporation) was added to the suspension and allowed to act for five hours. The suspension was then heat treated at 70° C. for 20 minutes, after which it was separated by a centrifuge into a fraction of primarily cell walls and a fraction of primarily protein. A component of primarily protein was then dried to obtain 388 g of yeast protein. Protein content of this yeast protein was measured using the Kjeldahl method to give a protein content of 62%.

Embodiment 6

One kilogram of dried fungal bodies of brewer's yeast derived from *Saccharomyces cerevisiae* culture yeast were suspended in water and heat treated at 90° C. for 20 minutes. A residue left after extracting an extract portion with a centrifuge was suspended in water at a concentration of 10%, then was adjusted to 40° C. and a pH of 6.0, after which 3 g of a cell wall lytic enzyme ("Denatyme GEL," manufactured by Nagase ChemteX Corporation) was added to the suspension and allowed to act for five hours. The suspension was then heat treated at 70° C. for 20 minutes, after which it was separated by a centrifuge into a fraction of primarily cell walls and a fraction of primarily protein. The fraction of primarily cell walls was then dried to obtain 201 g of a yeast cell wall fraction. Dietary fiber content of this yeast cell wall fraction was measured using an enzymatic-gravimetric method (Japan Food Research Laboratories value) to give a dietary fiber content of 53%. Meanwhile, a fraction of primarily protein was dried to obtain yeast protein. The yeast protein was adjusted to a concentration of 10% in water suspension, then was adjusted to 45° C. and a pH of 8.0, after which 7 g of a protease (PROTIN NY-100, manufactured by Amano Enzyme Inc.) was added to the suspension and allowed to act for five hours. A residue was then removed by centrifugation and the supernatant obtained was concentrated and spray dried to obtain 330 g of a powdered seasoning. Nitrogen content of this seasoning was measured using the Kjeldahl method to give 11.2%.

Embodiment 7

Embodiment 7 was conducted in the same manner as embodiment 2, except that no heat treatment at 70° for 20 minutes was performed after the cell wall lytic enzyme was allowed to act, and 215 g of yeast protein was obtained. Protein content of this yeast protein was measured using the Kjeldahl method to give a protein content of 83%. Meanwhile, 76 g of a yeast cell wall fraction was obtained. Dietary fiber content of this yeast cell wall fraction was measured using an enzymatic-gravimetric method (Japan Food Research Laboratories value) to give a dietary fiber content of 63 wt %. The yeast protein obtained was adjusted to a concentration of 10% in water suspension, then was adjusted to 45° C. and a pH of 8.0, after which 7 g of a protease (PROTIN NY-100, manufactured by Amano Enzyme Inc.) was added to the suspension and allowed to act for five hours. Residue was then removed by centrifugation and the supernatant obtained was concentrated and spray dried to obtain 200 g of a powdered seasoning. Nitrogen content of this seasoning was measured using the Kjeldahl method to give 13.2%.

Embodiment 8

In embodiment 7, more than half of the dietary fiber in the obtained yeast cell wall fraction was glucan and mannan. A β-1,3-1,6-glucan content was measured using an enzymatic-gravimetric method (MUSHROOM and YEAST BETA-GLUCAN ASSAY KIT, manufactured by Megazyme International Ireland) to give 31.5 wt %. This cell wall fraction was separated with a separation filtration membrane having a molecular weight cut-off of 13,000 ("Microza UF," manufactured by Asahi Kasei Chemicals Corporation), after which filtrate having a molecular weight of 13,000 or less was collected and further separation was performed with a separation filtration membrane having a molecular weight cut-off of 3,000 ("Microza UF," manufactured by Asahi Kasei Chemicals Corporation). Pigment components and mineral components contained in the filtrate were removed, and a low molecular weight β-1,3-1,6-glucan composition was obtained. A β-1,3-1,6-glucan content was measured using an enzymatic-gravimetric method (MUSHROOM and YEAST BETA-GLUCAN ASSAY KIT, manufactured by Megazyme International Ireland) to give 83.4 wt %.

Comparative Example 1

Comparative example 1 was conducted in the same manner as embodiment 1, except that 30 g of the cell wall lytic enzyme "Filtrase BRX" and 5 g of protease were allowed to act simultaneously. The process obtained 479 g of yeast protein from 1 kg of residue from which yeast extract had been extracted. The protein content of this yeast protein was measured using the Kjeldahl method to give a protein content of 48%. Meanwhile, 521 g of yeast cell wall fraction was obtained. The dietary fiber content of this yeast cell wall fraction was measured using an enzymatic-gravimetric, method (Japan Food Research Laboratories value) to give a dietary fiber content of 23%.

Comparative Example 2

One kilogram of "KR yeast" (manufactured by Kohjin Co., Ltd.) yeast cell bodies were adjusted to a concentration of 10% in water suspension, then were adjusted to 40° and a pH of 6.0, after which 10 g of a cell wall lytic enzyme ("Denatyme GEL," manufactured by Nagase ChemteX Corporation) and 20 g of a protease (PROTIN NY-100, manufactured by Amano Enzyme Inc.) were simultaneously added to the suspension and allowed to act for 5.5 hours at 50° C. A heat inactivation process was then performed at 90° C., after which residue was removed by centrifugation and the supernatant obtained was concentrated and spray dried to obtain 750 g of a powdered seasoning. Nitrogen content of this seasoning was measured using the Kjeldahl method to give 9.1%.

Evaluation Test 1

A 0.3% hot water solution was prepared for each of the powdered seasonings obtained in embodiments 2, 6, and 7 and in comparative example 2, and an organoleptic assessment of taste was conducted for each. A ten member panel conducted comparative evaluation of savoriness intensity, mellowness, intensity of detracting flavors, groundedness, and pleasantness for a water solution of each sample and a reference protein enzymolysis product. A number of panelists making a given determination is shown in Table 1. "Groundedness" is one element contributing to a flavor of richness and indicates body and a feeling of elevated flavor. "Fermented Umami Flavoring" (manufactured by Kikkoman) was used as the reference protein enzymolysis product.

TABLE 1

Organoleptic Evaluation of Simple 0.3% Hot Water Solution

| Comparison to reference protein enzymolysis product: | Embodiment 2 Seasoning | Embodiment 6 Seasoning | Embodiment 7 Seasoning | Comparative Example 2 Seasoning |
|---|---|---|---|---|
| Savoriness intensity | 4 | 3 | 4 | 3 |
| Mellowness | 9 | 7 | 9 | 4 |
| Detracting flavor intensity | 7 | 5 | 6 | 5 |
| Feels grounded | 9 | 7 | 8 | 3 |
| Pleasant | 8 | 6 | 8 | 3 |

Evaluation Test 2

Using the seasoning obtained in embodiment 2, a consommé soup was prepared in a mixture with the ingredients listed in Table 2. As a contrast, a consommé soup not combined with the seasoning was also prepared. A flavor comparison was also conducted with a reference protein enzymolysis product (fermented umami flavoring manufactured by Kikkoman) added. Comparative evaluations of each were given by a ten-member panel. In the results, ten of the ten panel members rated the consommé soup to which the seasoning of the present invention had been added as having a better flavor than the comparison consommé soup. When compared to the consommé soup to which the reference protein enzymolysis product had been added, savoriness was about the same, but the seasoning obtained in embodiment 2 imparted groundedness and mellowness to the consommé soup and was evaluated as more preferred in taste and coherency.

TABLE 2

Consommé Soup Recipe for 100 ml hot water

| Name of Ingredient | Control | Seasoning of Present Invention Sample | Reference Protein Enzymolysis Product Sample |
|---|---|---|---|
| Chicken powder | 1.25 g | 1.25 g | 1.25 g |
| Table salt | 0.75 g | 0.75 g | 0.75 g |
| Powdered onion extract | 0.5 g | 0.5 g | 0.5 g |
| Superfine sugar | 0.31 g | 0.31 g | 0.31 g |
| Powdered roasted onion extract | 0.13 g | 0.13 g | 0.13 g |
| Garlic powder | 0.01 g | 0.01 g | 0.01 g |
| White pepper | 0.01 g | 0.01 g | 0.01 g |
| Seasoning obtained in embodiment 1 | — | 0.05 g | — |
| Reference protein enzymolysis product | — | — | 0.05 g |
| Total | 2.96 g | 3.01 g | 3.01 g |

FIELD OF INDUSTRIAL APPLICABILITY

The yeast protein according to the present invention can be used as a non-allergenic protein as a substitute for wheat or soy bean protein. For example, the yeast protein can be used as an ingredient in processed meat products such as ham sausage and hamburger; in processed seafood such as kamaboko; in sweets such as cookies; or in bread, noodles, dumpling wrappers, and the like, and can also be used as an ingredient in seasoning. The yeast cell wall fraction according to the present invention can be used as a functional ingredient and as a physicality enhancer for food. For example, the yeast cell wall fraction can be utilized as a water retaining agent or shape retaining agent, a freezing/thawing resistance agent, or a drip prevention agent in processed meat products and frozen foods, and also as various dietary fiber ingredients. Furthermore, the yeast cell wall fraction can also be utilized as a functional ingredient of an immunostimulator, for example. In addition, a highly pure, low molecular weight β-1,3-1,6-glucan can be obtained through a simple separation/purification, and can be utilized as a health food or the like. The seasoning according to the present invention has a unique flavor and can be used similarly to typical protein enzymolysis products and yeast extracts. The seasoning can, for example, be blended as an ingredient in soy sauce, sauces, stock, and gravy, or as a seasoning in processed foods.

The invention claimed is:

1. A manufacturing method of a composition comprising a yeast protein, which method comprises:
    allowing a glucanase or a cell wall lytic enzyme to act on yeast cell bodies from which yeast extract has been extracted or yeast cell bodies that have not undergone yeast extract extraction,
    wherein the glucanase acts on the yeast cell bodies in the absence of a protease or the cell wall lytic enzyme acts on the yeast cell bodies at a temperature or pH at which protease is not active;
    removing a cell wall structural component; and
    obtaining the composition comprising the yeast protein, wherein the composition has a yeast protein content of 60% or more.

2. A manufacturing method of a yeast cell wall fraction containing 50 wt% or more of dietary fiber, which method comprises:
    allowing a glucanase or a cell wall lytic enzyme to act on yeast cell bodies from which yeast extract has been extracted or yeast cell bodies that have not undergone yeast extract extraction,
    wherein the glucanase acts on the yeast cell bodies in the absence of a protease or the cell wall lytic enzyme acts on the yeast cell bodies at a temperature or pH at which protease is not active;
    removing a fraction of primarily protein; and
    obtaining a cell wall fraction containing 50 wt% or more of dietary fiber.

3. The manufacturing method according to claim 1, wherein the glucanase is *Streptomyces*-derived.

4. The manufacturing method according to claim 1, wherein the glucanase or the cell wall lytic enzyme is allowed to act, then a heat treatment is performed at 50° C. or more for five minutes or more, after which the cell wall structural component is removed.

5. The manufacturing method of the yeast cell wall fraction according to claim 2, wherein the glucanase or the cell wall lytic enzyme is allowed to act, then a heat treatment is performed at 50° C. or more for five minutes or more, after which a cell wall structural component is removed.

6. A method of manufacturing a yeast-derived seasoning, comprising:
    obtaining the composition comprising a yeast protein according to the method of claim 1; and
    contacting the yeast protein with a protease and allowing the protease to enzymatically degrade the yeast protein to obtain the yeast-derived seasoning;
    wherein the seasoning obtained by the enzymatic degradation of the yeast protein by the protease has a solid content with a total nitrogen content of 11% or more.

* * * * *